United States Patent [19]

LeRoy et al.

[11] 4,172,449
[45] Oct. 30, 1979

[54] BODY FLUID PRESSURE MONITOR

[75] Inventors: Pierre L. LeRoy; Walter M. Bruner, both of Wilmington, Del.

[73] Assignee: New Research and Development Laboratories, Inc., Wilmington, Del.

[21] Appl. No.: 901,343

[22] Filed: May 1, 1978

[51] Int. Cl.² ............................................. A61B 5/00
[52] U.S. Cl. .................................... 128/654; 128/748
[58] Field of Search .......... 128/2 A, 2 R, 2 S, 2.05 E; 73/729, 730, 732

[56] References Cited

U.S. PATENT DOCUMENTS

| 3,625,199 | 12/1971 | Summers | 128/2.05 E |
| 3,977,391 | 8/1976 | Fleishmann | 128/2 A |
| 4,006,735 | 2/1977 | Hittman et al. | 128/2 A |
| 4,022,190 | 5/1977 | Meyer | 128/2 A |

FOREIGN PATENT DOCUMENTS 2125349  12/1972  Fed. Rep. of Germany ...... 128/2.05 E

OTHER PUBLICATIONS

DeJong et al., "Biotelemetry", vol. 2, No. 5, 1975, pp. 257–264.
DeLange et al., Translation of "Zeitschrift for Kinderchirurgie", Band 22, Dec. 1977.

*Primary Examiner*—William E. Kamm
*Attorney, Agent, or Firm*—Connolly and Hutz

[57] ABSTRACT

Body fluid pressure is monitored by implanting a sensor in the body which is responsive to the pressure therein. The sensor communicates with radiopaque means which changes its position when there is an abnormal amount of pressure as compared to a normal amount of pressure whereby the change can thereby be detected by X-Ray and translated into a value indicative of the pressure, thereby permitting serial, comparative, reliable and permanent recording in a relatively inexpensive manner.

10 Claims, 9 Drawing Figures

BODY FLUID PRESSURE MONITOR

BACKGROUND OF THE INVENTION

Many diseases are associated with abnormal pressure changes. Early detection of these changes is therefore important. At present the current state of the clinical medical art is to be able to detect only advanced pressure changes due to progression of frequently fatal disease processes. Accordingly, there is a need for early detection implantable devices to assess and follow changes in both acute and chronic references based in terms of days to years, and to provide a serial, comparable method for permanent recording and comparison. Such pressure monitoring systems require three stages: sensor, transducer, and quantitative recording.

The invention is concerned with devices for monitoring the pressure of various body fluids, such as in the central nervous system, genito-urinary and cardiovascular systems. One important application of such devices is the measurement of intracranial pressure. It is desirable to determine, for example, if an abnormal amount of pressure exists in such areas as the bladder, vena cava, intracranial ventricles and under the dura in the cranial cavity, and other areas. Various practices have been attempted with varying degrees of success for measuring such body pressure.

To date the methods used in the art are based on direct puncture and hydraulic measurement methods; implantable devices using a balanced force principle; piezo-electric crystal; fiberoptic pressure sensing; or radioactive detection chamber. All of these practices have serious disadvantages such as high cost.

There is a need to provide a reliable body pressure monitor which controls problems attendant with the prior art such as drift. There is further a need to provide such a monitor which can be utilized with minimum inconvenience to the patient a repeated number of times. There is likewise a need for a monitor which also provides a permanent record of the information upon which the body fluid pressure measurements are taken.

SUMMARY OF THE INVENTION

An object of this invention is to provide such a body fluid pressure monitor which fulfills the above needs.

A further object of this invention is to provide a novel device which may be implanted in the patient and left therein so as to permit subsequent pressure measurements to be taken.

A yet further object of this invention is to provide a simplified method of monitoring the body fluid pressure as indicated above with a minimum invasion of the body areas.

In accordance with this invention the implantable fluid pressure monitoring device includes radiopaque material so that changes in position of the device resulting from changes in the body fluid pressure can be measured by means of X-Rays for translating these changes into information used for determining pressure differentials.

The invention is preferably practiced by including a device which incorporates a means sensitive to transfer of fluid exposed to the body fluid for sensing the amount of pressure and for transmitting some indication of that amount to a detector which includes radiopaque components in such a manner as to result in the components having a change in position when there is an abnormal amount of pressure as compared to a normal amount of pressure. The X-Ray serves as a permanent record for comparison and serial study methods.

THE DRAWINGS

DETAILED DESCRIPTION

In general this invention is practiced utilizing implantable devices which contain radiopaque components, the change of relative position or shape of which monitors body fluid pressure when X-Rayed or when sensed by X-radiation. The inventive arrangements have the advantages of reliability, low cost when compared to conventional electronic and other current monitoring devices and also permit a generally permanent implantation in the body thus avoiding removal operations, while also offering a means for serial, comparative pressure measurement at any desired time.

Figure 1:
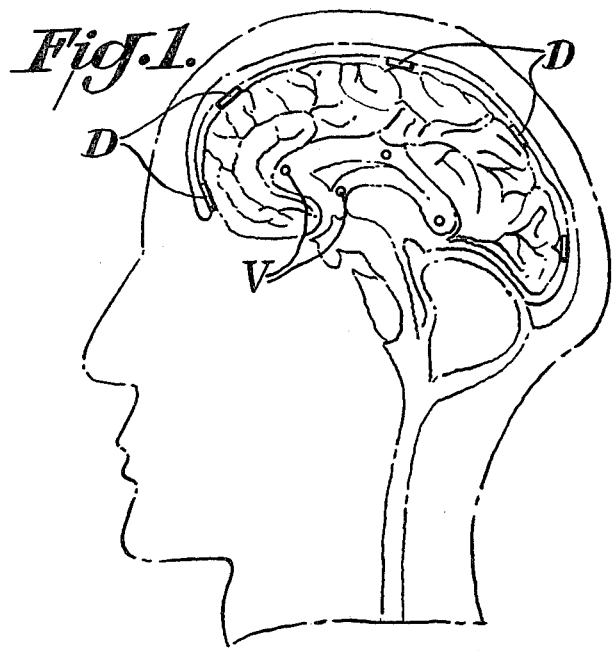
FIG. 1 is a schematic view of a human head showing various locations where the pressure monitoring device of this invention may be used.

FIG. 1 exemplifies some of the locations where a pressure monitoring device of the invention may be used. As indicated therein, for example, the device may be mounted at various locations D over or under the dura in the cranial cavity or as indicated by V in the fluid containing ventricles. The invention, however, is not limited to such specific locations but may be practiced by monitoring pressure in various other areas having body fluids such as the vena cava, the bladder or other cavities.

For the sake of simplicity in FIG. 1 a tube exposed to the body fluid is illustrated as in the ventricles while the tambour-type implants are illustrated under the dura in the cranial cavity. The various embodiments hereinafter described generally include such sensors or tubes and detectors or tambours although the structure thereof may take different forms. As later described, the sensor may also be connected by fluid means to other sensors more remotely located for convenience.

Figures 2, 3:
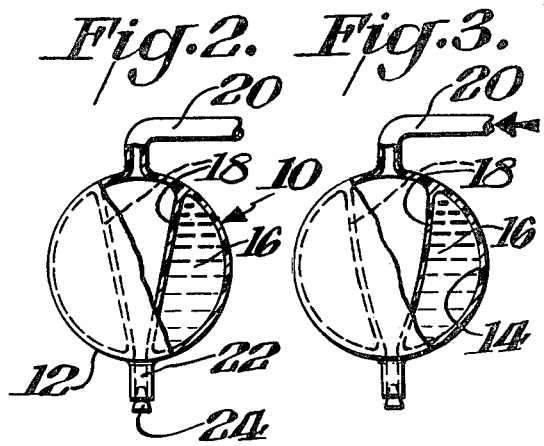
FIG. 2 is an elevation view partly in section of a pressure monitoring device in accordance with one aspect of this invention in its normal pressure indicating condition.
FIG. 3 is a view similar to FIG. 2 in its abnormal pressure indicating condition.

FIGS. 2-3 illustrate one form of this invention wherein monitor device 10 includes an implantable device having a body 12 of curvilinear configuration containing a fluid tight compartment or compartments 14 which in turn contain radiopaque fluid 16. The compartments 14 are bounded on at least one side or part of their inner surface area in the illustrated embodiment by a flexible membrane 18 or multiple membranes capable of moving under body fluid pressure. Compartments 14 separated by the membranes 18 are exposed to the body fluid by means of an orifice or tube 20. Tube 20 thus leads to the passageway formed by membranes 18 in the tambour-like device 10 with the downstream end of the passageway having a tube 22 which may be used for fluid egress or may have a plug 24. FIG. 2 shows the condition of device 10 under normal pressure. This position can be detected and recorded by taking an appropriate X-Ray of the patient. Tube 20 may, for example, have its upstream end in the ventricle with the tambour itself situated at a more convenient location. If there is an abnormal pressure at the situs being monitored such as the ventricle the increase in pressure from the fluid entering tube 20 causes membranes 18 to bow outwardly thus changing the configuration of compartments 14 as shown in FIG. 3. Since compartments 14 are filled with radiopaque fluid 16, a suitable X-Ray will detect and record the change in condition. Thus, the use of the radiopaque fluid 16 permits the convenient monitoring of the body pressure to be accomplished by a simple X-Ray procedure, fluoroscopy, computerized tomography or CAT scan.

An alternative device may be used for practicing the invention along the lines of the device of FIGS. 2-3 except that in the alternative device the diaphragm or membrane itself would be radiopaque or contain radiopaque components such as a bead chain. Thus, the flexible membrane would actively move under small forces to, in turn, change the location of the radiopaque components thereby obviating the need for radiopaque fluid. The embodiment illustrated in FIGS. 4-6 works generally along these principles.

Figure 4:
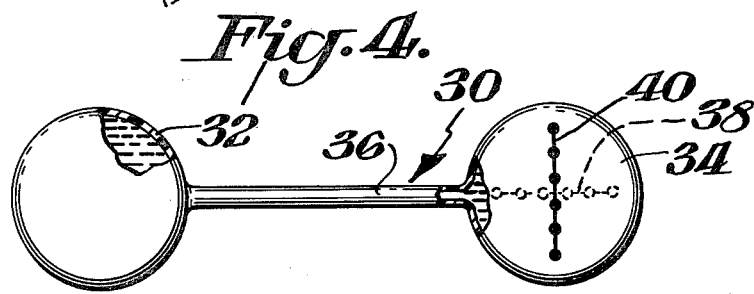
FIG. 4 is a plan view partly in section of a further pressure monitoring device in accordance with this invention.
Figure 5:
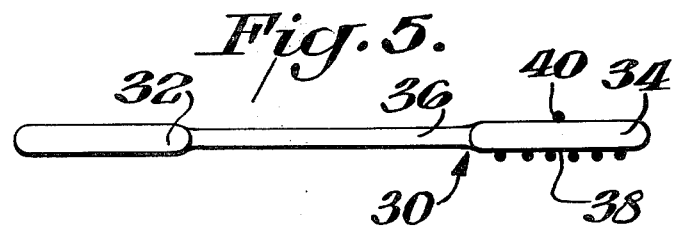
FIG. 5 is a side elevational view of the device of FIG. 4 in its normal pressure indicating condition.
Figure 6:
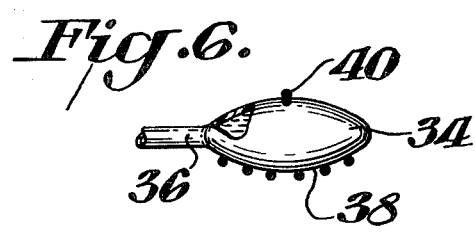
FIG. 6 is a side elevation view similar to FIG. 5 of a portion of that device in its abnormal pressure indicating position.

FIGS. 4-6 show a further embodiment of this invention wherein the device 30 includes a fluid containing sensing tambour 32 and a detecting tambour 34 interconnected by tube 36 so that fluid may move freely from one tambour to the other thereby detecting pressure changes. In practicing this embodiment of the invention fluid filled tambour 32 would be implanted within the body such as the intracranial cavity and is capable of responding to external fluid pressure on its sides or faces. The response to the pressure changes results in fluid being transmitted to detector tambour 34. Detector tambour 34 may be positioned either within or outside the body and is equipped with a pair of bead chains 38, 40 embedded in the tambour diaphragm and able to change its shape or position in accordance with the distortion of shape of the tambour sides or faces. FIG. 4 illustrates the radiopaque or sensitive bead chains 38, 40 to be perpendicular to each other. Alternatively, the detector inside the body may be connected to a tap outside the body, useful for calibration, etc. FIG. 5 illustrates the condition of device 30 and more particularly detector 34 in the normal condition. This condition would be recorded by means of an appropriate X-Ray or gamma-detection system, even where detector 34 is mounted outside the body. FIG. 6 illustrates the condition of detector 34 when there is an abnormal pressure. By suitable X-Ray this condition would also be detected and recorded. The advantage of the use of X-Rays in this embodiment even where detector 34 is positioned outside the body is that a permanent record is made of the body pressure being monitored. Additionally, the permanent record or X-Ray affords the physician an opportunity to more accurately determine the amount of abnormal pressure by comparing distances on the X-Ray which would reflect the spacing between the bead chains 38, 40 with standard distances from a chart or comparative X-Ray under normal conditions. Further, this comparison may be under ideal or more leisure conditions than under urgent circumstances which would otherwise be required if a permanent record were not available.

Figure 7:
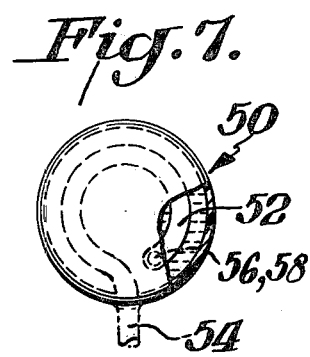
FIG. 7 is a plan view partly in section of yet another pressure indicating device in accordance with this invention in its normal pressure indicating condition.
Figure 8:
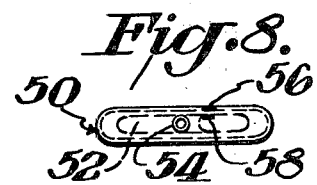
FIG. 8 is an elevation view of the device of FIG. 7.
Figure 9:
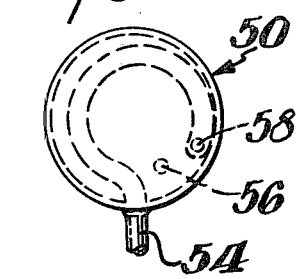
FIG. 9 is a plan view of the device of FIGS. 7-8 in its abnormal pressure indicating condition.

FIGS. 7-9 illustrate yet another embodiment of this invention. As indicated therein, the single tambour-like device 50 is implantable within the body and includes in the tambour a pressure responsive device such as a Bourdon tube 52. Bourdon tubes generally function as pressure gauges by forming a hollow tube usually of elliptical cross-section bent into an arc of over 180°. One end of a Bourdon tube is closed and fluid is admitted into the open end. The admission of the fluid causes the curved tube to become less curved under increased pressure. Thus the change in curvature from the normal curve gives an indication of the pressure in the tube. The action of a Bourdon tube depends on the fact that the pressure tends to increase the volume of the tube. Since a circular cross-section allows more volume than an elliptical one for a given periphery the section will tend toward the circular form under increased pressure which in turn will cause the change in the shape of the tube. It is for this reason that elliptical cross-sections are preferred. Bourdon tubes are well known and discussions thereof may be found in many technical publications.

In the illustrated embodiment Bourdon tube 52 includes at its upstream end tube section 54 which would ultimately be exposed to the body fluid at the situs in the patient being monitored.

In accordance with the invention illustrated in FIGS. 7-9 the invention is practiced by using radiopaque buttons or droplets, the spacing of which would be varied in accordance with the position of the Bourdon tube. For example, FIG. 8 illustrates a fixed button 56 to be located on the tambour body superimposed above button 58 on the Bourdon tube. FIG. 9 illustrates the condition when there is an abnormal pressure whereby button 58 is moved away from being superimposed with respect to button 56. The locations of buttons 56, 58 may vary bearing in mind that one button should be fixed by being mounted on a suitable location of the tambour body while the other button would be movable by being secured to the Bourdon tube and thus responsive to and reflective of changes in pressure. By appropriate X-Ray, of course, the relative positioning of the buttons would be sensed and recorded.

A variation of the device shown in FIGS. 7-9 may include instead of a single opening tube, a tube attached to device 50 which in turn would be attached to a tee connector and thence to another body cavity or outside the body.

All of the exemplified embodiments of this invention may be used in multiple form to provide a global pressure monitoring device.

Where openings have been shown in the various devices for leading to the fluid being pressure monitored, the openings may be located with some advantage at the lower or bottom edge of the device when the device is implanted or located. Suitable flaps may be attached for suturing in the desired attitude.

The practice of this invention is particularly advantageous since it fulfills the objects hereinbefore stated. Additionally, the use of X-Rays provides a permanent record which may be referred to for determining under more ideal conditions the amount of pressure by being able to refer to the X-Ray. With properly calibrated sensors, the determination of abnormal pressure may be made by reference to standard charts or by reference to X-Rays showing normal conditions. The latter can be done by simply superimposing such X-Rays. The invention may also be practiced with devices which are distinctly more economical than prior art practices. For example, the use of the embodiment using a Bourdon tube may cost less than one-tenth the cost of prior art devices. Moreover, prior art devices are generally subject to drift of calibration, mechanical pressure leaks and are presently accessible only in research—medical centers, whereas clinical X-Ray facilities with which the invention would be used are readily globally available.

What is claimed is:

1. A device for monitoring body fluid pressure such as intracranial pressure and the like comprising a body member, said body member incorporating radiopaque components, said body member having pressure sensing means implantable within a living patient at the situs to be monitored and exposed to the body fluid thereat, and transmitting means between said pressure sensing means and said radiopaque components for causing said radiopaque components to be moved from a first pressure indicating position to a second pressure indicating position when said pressure sensing means is exposed to a change in pressure whereby the change in pressure may be detected and recorded by X-Raying said radiopaque components in accordance with the change in position thereof.

2. The device of claim 1 wherein said body member is a tambour.

3. The device of claim 2 wherein said pressure sensing means is a tube leading to said tambour.

4. The device of claim 3 wherein said tambour includes at least one compartment, a flexible membrane comprising at least one wall of said compartment, and said flexible membrane being in fluid communication with said tube whereby the position of said flexible membrane is determined by the fluid pressure thereagainst.

5. The device of claim 4 wherein said radiopaque components comprise radiopaque fluid in said compartment.

6. The device of claim 4 wherein said radiopaque components are attached to said flexible membrane.

7. The device of claim 2 wherein said radiopaque components comprise a first radiopaque bead chain on one face of said tambour and a second radiopaque bead chain perpendicular thereto on a face of said tambour opposite said one face, said tambour comprising a detector tambour having fluid therein, said pressure sensing means comprising a sensor tambour having fluid therein, and said transmitting means comprising a tube interconnecting said sensor tambour and said detector tambour whereby the fluid may pass therethrough.

8. The device of claim 3 including a Bourdon tube in said tambour, and said radiopaque components being on a relatively fixed portion of said tambour and on a relatively movable portion of said Bourdon tube.

9. In a process for monitoring body fluid pressure including the steps of implanting a pressure sensor within a living patient at the situs to be monitored, exposing the sensor to the pressure of the body fluid at that situs, transmitting pressure from the sensor to radiopaque components for causing the radiopaque components to change their relative position when there is a comparative change in pressure, and taking an X-Ray of the radiopaque components to provide a record and indication of the change in position whereby the corresponding change in pressure may be determined thereby.

10. In the method of claim 9 including mounting a plurality of sensors at different sites in the body to provide global pressure monitoring.

* * * * *